United States Patent [19]

Fiorenzano, Jr.

[11] Patent Number: 5,326,543
[45] Date of Patent: Jul. 5, 1994

[54] PROCESS, INSTALLATION AND CHAMBER FOR REDUCING BIOLOGICAL ACTIVITY IN AN ENCLOSURE, PARTICULARLY FOR A STORAGE SPACE

[75] Inventor: Alintor Fiorenzano, Jr., Rio de Janeiro, Brazil

[73] Assignee: Clover Electronica LTDA., Brazil

[21] Appl. No.: 65,891

[22] Filed: May 25, 1993

Related U.S. Application Data

[63] Continuation of Ser. No. 693,158, Apr. 29, 1991, abandoned.

[30] Foreign Application Priority Data

Oct. 1, 1990 [BR] Brazil .................. PI9004909

[51] Int. Cl.$^5$ .................................. A61L 9/00
[52] U.S. Cl. ............................ 422/292; 34/77; 34/219; 422/32; 422/40
[58] Field of Search .......... 422/4, 24, 29, 32, 40, 422/186.07, 186.10, 186.15, 292; 34/219, 225, 231, 233, 77; 219/390, 400; 392/356, 360, 494, 485, 379

[56] References Cited

U.S. PATENT DOCUMENTS

| | | | |
|---|---|---|---|
| 1,310,511 | 7/1919 | Summers | 422/4 |
| 1,701,096 | 2/1929 | Bowling et al. | 392/356 |
| 2,203,188 | 6/1940 | Beer | 422/4 |
| 2,343,338 | 3/1944 | Steel | 422/4 |
| 2,716,289 | 8/1955 | Lauck | 34/27 |
| 2,799,947 | 7/1957 | Elwess | 34/15 |
| 3,575,582 | 4/1971 | Covault | 392/356 |
| 3,654,432 | 4/1972 | Dyre | 392/492 |
| 3,659,096 | 4/1972 | Kompanek | 422/24 |
| 3,897,210 | 7/1975 | Gruber et al. | 422/31 |
| 3,934,355 | 1/1976 | Weibull | 34/46 |
| 4,079,233 | 3/1978 | Heywald | 392/360 |
| 4,124,467 | 11/1978 | Pincon | 204/157.5 |
| 4,134,216 | 1/1979 | Stevens | 34/77 |
| 4,205,456 | 6/1980 | Ayers et al. | 34/35 |
| 4,680,498 | 7/1987 | Fester | 392/356 |
| 4,857,277 | 8/1989 | Broomfield | 422/186.07 |
| 4,877,990 | 10/1989 | Fiorenzano, Jr. | 392/465 |
| 4,882,129 | 11/1989 | Andrews et al. | 422/186.2 |
| 5,037,618 | 8/1991 | Hager | 422/186.03 |

FOREIGN PATENT DOCUMENTS

90/02572 3/1990 World Int. Prop. O. .

Primary Examiner—Jill A. Johnston
Assistant Examiner—Laura E. Collins
Attorney, Agent, or Firm—Beveridge, DeGrandi, Weilacher & Young

[57] ABSTRACT

The storage life of cereal grains or other products is extended by reducing biological activity in the storage enclosure. Air is oxidized in a chamber which is external to the storage enclosure. The oxidized air is propelled from the oxidizing chamber to the storage enclosure. Oxidation of the air may be produced by heat, ultra-violet radiation, or catalyzation. Heating may be done in a block provided with anodes for dissipating electrostatic charges. After being heated, the air is cooled before it is propelled to the storage enclosure. When air is oxidized by ultra-violet radiation, it is processed by an ozone decomposition system before it is admitted to the storage enclosure.

12 Claims, 3 Drawing Sheets

PROCESS, INSTALLATION AND CHAMBER FOR REDUCING BIOLOGICAL ACTIVITY IN AN ENCLOSURE, PARTICULARLY FOR A STORAGE SPACE

REFERENCE TO RELATED APPLICATION

This is a continuation of application Ser. No. 07/693,158 filed Apr. 29, 1991, now abandoned.

BACKGROUND OF THE INVENTION

The present invention refers to a process, an installation and a chamber for reducing the biological activity in storage spaces, such as silos, storage sheds, grain stores, cargo holds in grain transport ships or the like, and particularly for the storage and preservation of grains or other perishable foodstuffs.

The storage of large quantities of agricultural products and principally cereals is problematic with regard to the preservation of the product throughout the period of storage. Losses due to the deterioration of stored grains has been a considerable problem on a worldwide scale and it should be observed that losses of this nature are presently of the order of 30% of the total product stocked in Brazil, about 12% in the USA and as high as 50% in some countries of the African continent.

Cereals are characterized by a high potential energy content. Their availability in thousands of tons makes storage locations an excellent nutrition medium for fungi, bacteria, acarids and insects, provided that the ambient conditions such as temperature and humidity (absolute humidity of the grain and relative humidity of the atmosphere) are favorable. The processes used up to the present involve a storage system which controls such parameters so as to reduce biological activity to a minimum. The controls act on the following variables:

Reduction of the absolute humidity of the grain by previous drying.

Constant airing of the storage ambient so as to reduce the fungi population by entertainment of the spores and to reduce the temperature increased as a result of biological activity.

Utilization of gases such as nitrogen (N2), carbon dioxide (CO2) and other gases with the basic purpose of reducing the concentration of oxygen and thus producing a reduction in the aerobic organisms population as well as the metabolism of the grain itself.

Use of toxic chemical products to reduce the amount of microorganisms and insects by intoxication.

All these processes have limited efficiency and some present health risks to the consumers, particularly those related to the use of toxic chemical products.

According to the most recent scientific works regarding the inter-relation of the various variables within a mass of cereals, fungi have been identified as one of the most important elements in the matrix of the echo-system. The following works can be cited as being of special importance: 1) Sinha R.N., Van Bronswijk J.E.M.H., Wallace H.A.H., C.M.A. Journal, Aug. 1, 1970, Vol. 103, 300-301 2) Sinha R.N., Van Bronswijk J.E.M.H., Environm. Entomology 2: 142, 1973 3) Sinha R.N., Journal of Economic Entomology, Vol 64, 1, 3-6. 4) Mori M., Onoue Y., Takahashi T., Chounan S., Moriya K., J Antibact. Antifung. Agents Vol. 15 N° 12, P 601 -605, 1987. 5) Griffiths A.D., Hodson A.C., Christensen C.M., Journal of Economic Entomology, Vol. 52, N° 3, pag. 516-518. 6) Sinha R.N., Harasymek L., Enviromental Entomology Vol 3, N° 2, pags. 244, 246. 7) Tadros, M.S., Vestnik Ceskoloveniske Spolecnosti Zoologicke, Svazek XXXIX, Cislo 4, 1975, Str. 293-296.

The above works show that the elimination of fungi in the stored mass results in the reduction over a period of time of the population of insects and acarids. It is important to note that not only fungivorous organisms depend on fungi but also all larva which, after hatching of the eggs, need fungi to be able to create their digestive systems.

A device for oxidizing particles in suspension in air is already known from Brazilian patent PI 8302255 (U.S. Pat. No. 4,877,990) and European patent 281.551 of the present inventor. Such device creates the generation of high power density within ducts provided in a refractory ceramic block by means of a resistance wire passing through such ducts. These devices are suitable for small and medium sized ambients but are not specially adequate for large areas, such as large stores for the stocking of grain.

Brazilian patent application PI 8502832 of the present inventor discloses a system for the preservation of agricultural products by sterilizing the air. That system uses U-shaped pipes or tubes inside silos, each tube being formed with various orifices in both of its vertical arms and one of the arms having in its interior an apparatus of the type disclosed in Brazilian patent PI 8302255 (U.S. Pat. No. 4,877,990). Such a system, however, was found to have the following disadvantages:

reduced preservation capacity per apparatus: the maximum amount with which satisfactory results of air sterilization were obtained is limited to about 200 kg of stocked product per apparatus;

grain damage: heat generation within the silo tends to dehydrate the stocked grain, thus prejudicing its preservation; and necessity to adapt the interior of the silos: the same number of U-shaped pipes as of the necessary apparatuses has to be installed within the silos.

Another disadvantage of the prior art grain storage systems is related to the generation of static electricity in view of friction between individual grains, in particular at the time of storage, and this may generate discharges that can cause explosions should there be any inflammable gases in the silo or shed, or even serious injury or death to persons within the silo.

Considering the prior art, the object of the present invention is to eliminate fungi from storage ambients so as to permit agricultural products to be preserved without the use of chemicals, as well as to permit the storage of the product with high absolute humidity content, in a totally new manner and without damaging the sorted grain.

A further object of the invention consists in eliminating the electrostatic charge in the stored product so as to avoid the resulting disadvantages and risks.

The process by which the above objects may be reached is characterized by the following steps:

gradually extracting the air from the ambient; ambient;

oxidating air within a chamber located outside the ambient;

forcing the processed air into the ambient.

The above process may be applied in closed, open or mixed circuit, that is to say, the air may circulate permanently without exchange with the atmosphere, or fresh processed air may be admitted to the ambient together with total removal of the air previously within the ambient, or further, part of the air may be circulated and the rest admitted from outside.

The use of as closed circuit, however, has the advantage that the air of the storage ambient is gradually sterilized with respect to the presence of microorganisms until almost total sterilization is obtained. Apart from this, a closed circuit permits one to obtain a hydrostatic balance between the air and the stored product.

The new concept presently proposed consists in introducing to the storage ambient regular volumes of sterilized air, sterilization being obtained by subjecting the air to elevated temperatures, of the order of 500° C,. and subsequently cooling the air before it is pumped into the storage ambient. The air is heated in such a manner that heat is not dissipated within the storage ambient, so as to permit temperature and humidity conditions to be maintained within the desired parameters.

SUMMARY OF THE INVENTION

The installation of the invention comprises:
an air line;
a chamber provided with an air entrance and an air exit, connected to the enclosure through said air line, said chamber including means for oxidizing air;
propelling means connected to said air line for introducing the air processed in said chamber to said enclosure.

Preferably, the air line establishes a closed circuit leaving an upper region of the storage enclosure, passing through the chamber, a heat exchanger and the propelling means and re-entering the storage enclosure at a lower region thereof, thus creating air circulation through the stored product.

In a preferred embodiment of the invention, the chamber is provided with one or more ceramic blocks therein having a series of capillaries through which a resistance wire passes to act as a heating filament.

According to the invention, it is possible to neutralize the electrostatic charge on the stored grains by suitable polarization of the heating filaments of the ceramic element. This polarization is obtained by using the thermionic emission effect which favors the neutralization of the positive electrostatic charges generated by friction between the individual grains, thus eliminating the risks resulting from the accumulation of such charges.

In an alternative system, the chamber is equipped with ultra-violet (UV) lamps. This embodiment makes the heat exchanger unnecessary, but it is then advisable to include a system for decomposing the ozone generated by the UV generation downstream of the chamber. Such a system may comprise an ozone trap or an air heating chamber for heating air to about 70 to 80° C. Obviously, however, there will be no necessity to decompose the ozone if the stored product is ozone-resistant or, for any reason, the presence of ozone is desirable.

Ultra-violet oxidation is indirect, that is to say, ultra-violet radiation degrades the protein casing of microorganisms or spores by ionization. The radicals thus liberated react with the components of the air to effect the neutralization.

BRIEF DESCRIPTION OF THE DRAWINGS

The invention will now be described in more detail with reference to an embodiment illustrated in the drawings. The figures show schematically.

DETAILED DESCRIPTION

Figure 1:
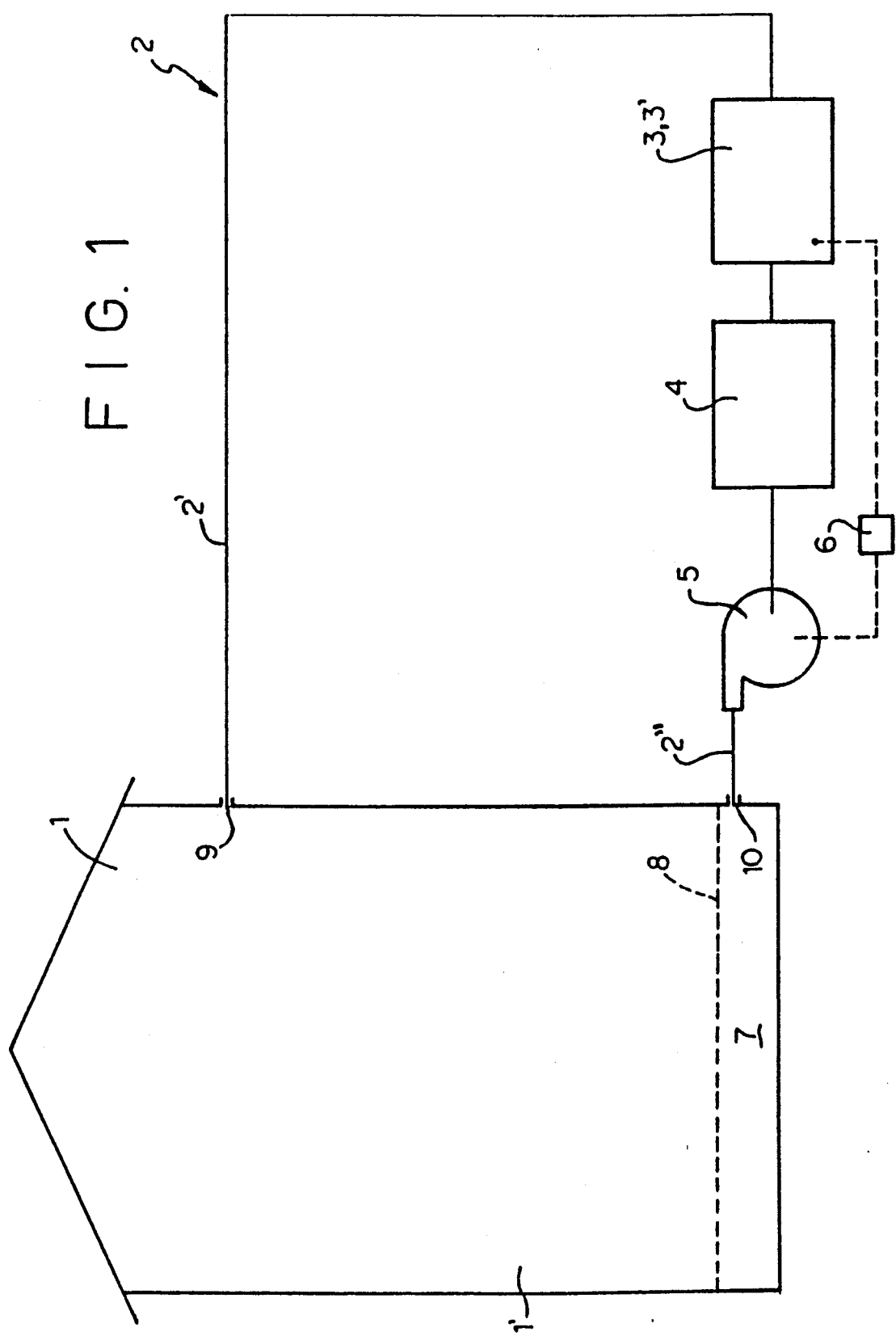
FIG. 1—a microbiological activity reducing installation in accordance with the present invention.

FIG. 1 shows a silo 1 in the upper portion of which there is an air outlet 9 to which an air line 2 is connected. The air line passes consecutively through an adiabatic a heating chamber 3, a heat exchanger 4 and propelling means or blower 5 which promotes the circulation of the air through line 2, before returning to the silo 1 through an air inlet 10 in a lower portion thereof. Between the air inlet in silo 1 and a storage chamber, there is a plenum chamber 7 and a perforated base or screen 8. Sterilized air is uniformly distributed in the plenum chamber 7 below the stored grain and it penetrates upwardly the storage compartment through the perforated base 8 so that the complete mass of grain is permeated by processed air.

The air inside silo 1 is sucked through air outlet 9 and, after processing, returns through inlet 10. The portion 2' of air line that is upstream of blower 5 represents the low pressure section of the line, whereas portion 2" is its high pressure section.

Air is heated in heating chamber 3 to a sufficiently elevated temperature to oxidize any microorganisms suspended in the air. This oxidation may be effected by heating, radiation or catalysis and chamber 3 may comprise a plurality of blocks of ceramic provided with heating elements, as will be described later with reference to FIG. 2, a series of ultraviolet lamps (FIG. 5) or a platinum catalyst (FIG. 6) for oxidizing viable particles or, furthermore, it may make use of available steam or any other heated fluid from local utilities.

Such embodiments are only mentioned by way of example, it obviously being possible to use other oxidation means.

The heat exchanger 4 may be conventional with a coil through which air flows and around which flows cooling water. Naturally, provided they are suitably dimensioned, any other suitable types of known heat exchanger may be used, for example finned air cooled exchangers.

The propelling device 5 may comprise a known air pump, compressor or the like.

Reference number 6 indicates an electronic processor or control circuit for activating and deactivating the propeller device in dependence upon the conditions detected by a detector 16 (FIG. 2) provided within the heating chamber 3. The electronic control and the detector are known components.

Figure 2:
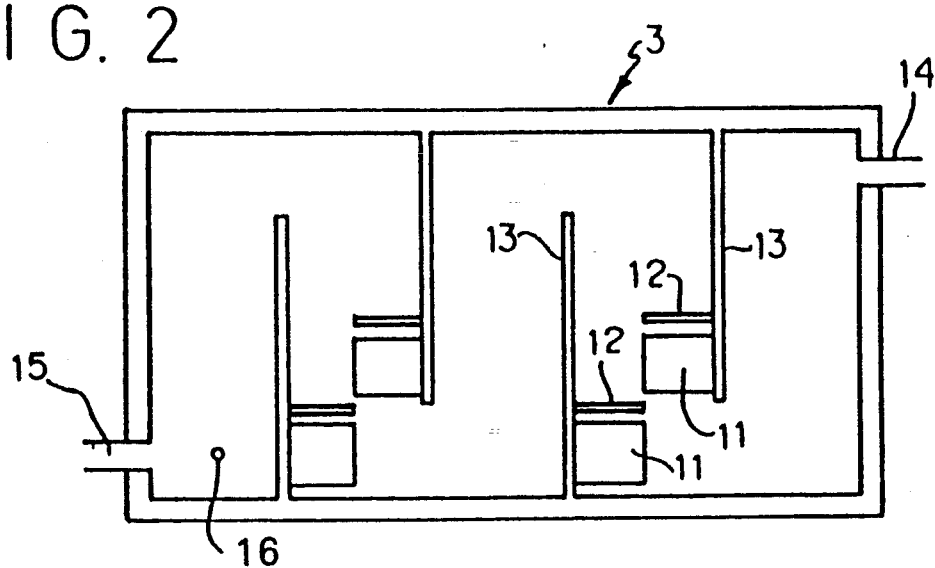
FIG. 2—a cross sectional view of a first embodiment of the chamber for oxidizing particles in the air.

FIG. 2 shows a heating chamber 3 provided with refractory ceramic blocks 11 and anodes 12 fixed to flow separating walls 13. Chamber 3 has an air inlet 14 and an air outlet 15, the separating walls 13 causing the air to follow an extended path so as to increase its residence time within the chamber. A greater residence time of the air within the chamber 3 favors a more complete elimination of the microorganisms in suspension.

Detector 16, which is shown only schematically, may be a thermo-couple type temperature sensor, or a suspended particle detector or, furthermore, an electrostatic charge detector. Known particle sensors comprise, for example, a semiconductor laser device (infrared), a suspended viable particle monitor (Tyndall effect) or a plate capacitor (variable capacitance).

The walls of chamber 3 are preferably thermally insulated from the atmosphere so that the air heats more rapidly and at a greater intensity and so that there are no significant heat losses.

Figure 3:
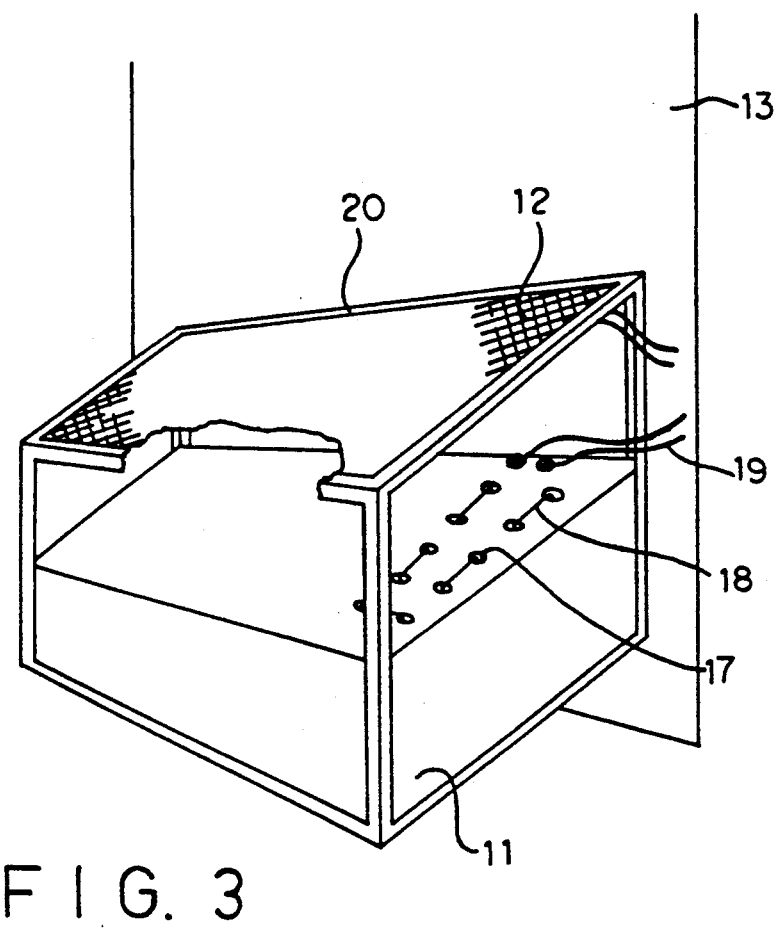
FIG. 3—a perspective view of a detail of the chamber of FIG. 2.

FIG. 3 shows in greater detail one of the ceramic blocks 11 and its corresponding anode 12. According to a principle analogous to that in the above mentioned Brazilian patent PI 8302255 (U.S. Pat. No. 4,877,990) and European patent 281.551, the ceramic block has a series of capillaries 17 through which a heating filament 18 passes. The terminals of the filament are indicated by reference 19. The temperature of the air flowing through the capillaries reaches about 500° C.

According to a preferred embodiment, anode 12 which is positioned immediately above the ceramic block, is polarized positively with respect to the filaments of the block and comprises a metallic net with a 5 mm mesh, mounted on an insulating support 20 of Teflon ® defined as polytetrafluoroethylene. The anode voltage should be chosen so as to avoid any corona effect, 1 kv being suitable for the desired purpose. The corona effect is particularly undesirable due to the resulting formation of ozone (03). The heat generated in the capillaries generates electron emission, this occurring as from about 300° C., anode 12 accelerating the electrons emitted.

Figure 4:
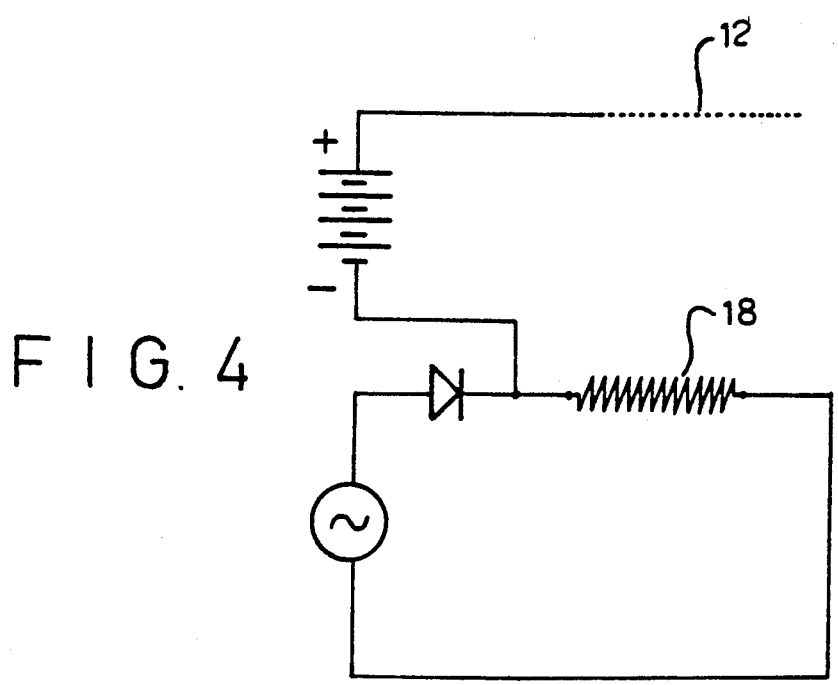
FIG. 4—a schematic representation of an electrical circuit for the embodiment illustrated in FIGS. 2 and 3.

FIG. 4 is an electric circuit exemplifying a manner of interconnecting filament 18 and anode 12 and showing how the latter may be polarized with respect to the former.

Figure 5:
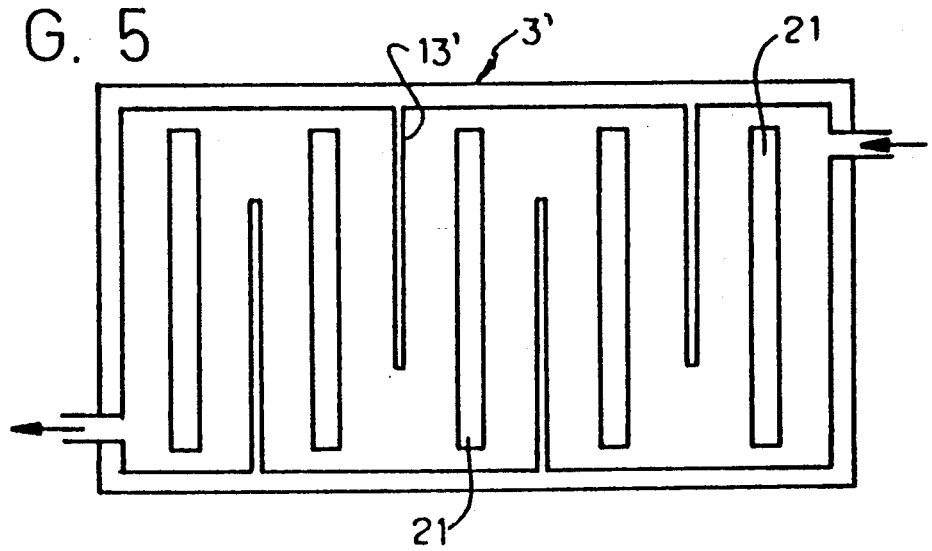
FIG. 5—a cross section of a second embodiment of the chamber for oxidizing particles in the air.

FIG. 5 shows an embodiment in which a chamber 3' is equipped with a series of ultra-violet lamps 21. In this embodiment, the flow separating walls may comprise a material having reflective properties, such as a polished metal or mirror, so as to increase the incidence of ultraviolet radiation on the particles suspended in the air flowing through the said chamber.

Figure 6:
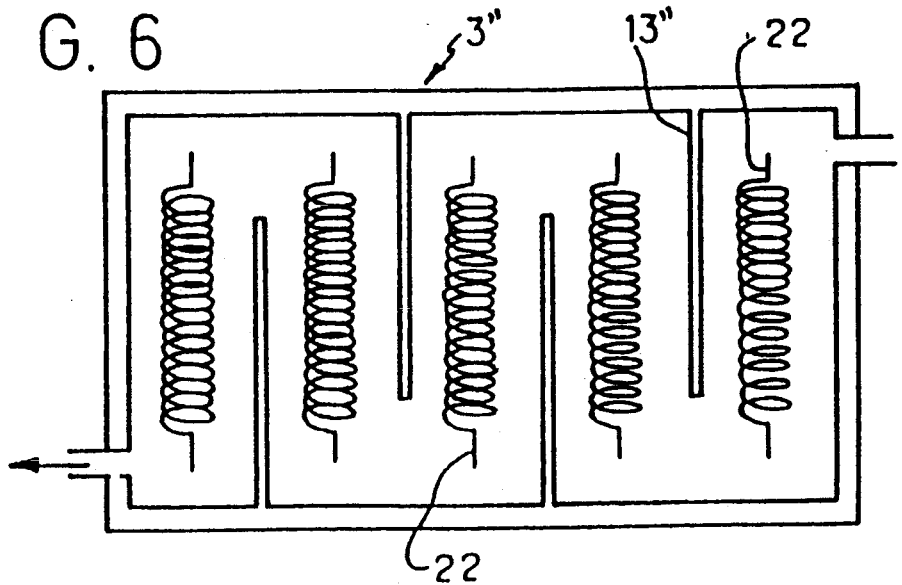
FIG. 6—a cross section of a third embodiment of the air particle oxidizing chamber.

The embodiment shown in FIG. 6 comprises a plurality of catalyzers 22 as oxidation elements. Such catalyzers 22 may be platinum pads and are connectable to an electric energy source (not shown).

On Aug. 9, 1990, a model Kepler-Weber silo was loaded with 70 tons of recently harvested corn without any type of prior treatment and having an absolute humidity of 18%. Under such conditions, the normal expectation is for the corn to be totally fermented in two weeks.

The system for the reduction of biological activity, comprising a heating chamber with refractory ceramic blocks, a water-cooled coil type heat exchanger and a propeller device, was regulated to process the total volume of air within the silo once every three hours, that is to say, the air was totally processed eight times a day.

Measurements were taken at 16 different points twice a day, and microbiological analysis was carried out in the fungus laboratory of the University of Sao Paulo (USP) by Dr. Valderez Gambali, vice-president of the Brazilian Society of Microbiology, whereas the analysis of the temperature, pressure and humidity within the system was carried out by the Kepler-Weber team.

On Sep. 19, 1990, that is to say, 40 days after the start of the experiment, the system was still functioning and the corn was in a perfect condition with the same average degree of 18% humidity, the maximum temperature within the silo being about 21° C., contrary to all the most conservative predictions. An increase of temperature due to biological activity in the mass of grain and loss of humidity due to heating would have been expected. This result was obtained without the customary prior drying of the grains of corn which would have consumed more energy, nor the application of any toxic or atoxic chemical product.

In Brazil, the fungus normally present in harvested corn is of the Fusarium type and during the period of storage, one would expect that this flora would change from Fusarium to a high incidence of Piniscilum and Aspergillus Flavus. In the above described experiment, no Piniscilum or Aspergillus was observed, and only a reduction in Fusarium and the total absence of insects, without the formation of any woodworm or the like, was observed.

The proposed system is modular and is easily adapted to any type of storage location, such as silos, warehouses, grain stores or ships' cargo holds, the choice of parameters such as flow rate, power consumption of the sterilization system, the type of heat exchanger, the static pressure of the propeller means and the polarization voltage, being selected basically as a function of the mass of material to be preserved as well as of the nature of the material and the desired absolute humidity. The tests carried out showed that the ratio power consumption to mass of product is in the region of 10 Watts/ton.

I claim:

1. Apparatus for reducing biological activity in a storage enclosure and keeping it low, for preserving the storage enclosure's contents against deterioration, comprising:
   a chamber in fluid communication with a storage enclosure, said chamber having an air inlet and an air outlet;
   oxidation means in said chamber for oxidizing air in said chamber;
   air line means connecting said chamber to said storage enclosure;
   propelling means in communication with said chamber for propelling oxidized air from said chamber to a storage enclosure; and,
   means for releasing air from said storage enclosure;
   said oxidation means for oxidizing air including at least one block which is provided with capillaries, a heating filament connectable to an electric energy source passing through said capillaries, said block being so arranged between said inlet and outlet of the chamber whereby at least part of the air that circulates in the chamber passes through the capillaries; and
   a heat exchanger means for cooling the air that leaves the chamber, said heat exchanger means being connected between the oxidation means and said storage enclosure.

2. Apparatus according to claim 1 wherein a closed circuit is provided for circulating air from said storage enclosure, through said chamber, through said heat exchanger, through said propelling means, and back to said storage enclosure.

3. Apparatus according to claim 1 wherein said heat exchanger means is provided in a flow path between the chamber and the propelling means.

4. Apparatus according to claim 1, wherein said storage enclosure is a silo with a lower chamber, a storage compartment and a perforated base; the lower chamber being situated below the storage compartment, the perforated base being provided between the lower chamber and the storage compartments.

5. Apparatus according to claim 1 wherein a detector is provided within the chamber, an electronic control circuit means connected to the detector for controlling the propelling means in dependence upon conditions monitored within the chamber.

6. Apparatus according to claim 1 wherein said detector is a temperature sensor.

7. An apparatus for reducing biological activity in storage enclosures and keeping it low, to preserve the storage enclosure's contents against deterioration, comprising a chamber in fluid communication with a storage enclosure, said chamber including air inlet means for admitting air into the chamber, air outlet means for supplying air from said chamber to the storage enclosure, at least one oxidation element which includes a block provided with capillaries, a heating filament connectable to an electric energy source passing through said capillaries, said block being arranged between said inlet and outlet means of the chamber, whereby at least part of the air that circulates in the chamber passes through the capillaries, an anode provided above the block, said anode being polarizable with respect to the filament by means of the application of an electric voltage.

8. An apparatus according to claim 7, wherein the anode includes a metallic screen mounted on an insulating support.

9. An apparatus according to claim 8, wherein the metallic screen of the anode has a mesh of about 5 mm.

10. An aparatus according to claim 9, wherein the insulating support is manufactured from polytetrafluoroethylene.

11. An apparatus according to claim 7, wherein the voltage applied to the anode is about 1 kv.

12. An aparatus according to claim 7, further comprising flow separating walls provided in said chamber which define partial compartments for one or more oxidation elements.

* * * * *